US005667765A

United States Patent [19]
Hansenne et al.

[11] Patent Number: 5,667,765
[45] Date of Patent: Sep. 16, 1997

[54] PHOTOPROTECTIVE/COSMETIC COMPOSITIONS COMPRISING AT LEAST ONE SOLID ORGANIC SUNSCREEN COMPOUND AND SALICYLATE SOLVENTS THEREFOR

[75] Inventors: Isabelle Hansenne; Victoria van Leeuwen, both of Paris, France

[73] Assignee: L'Oreal, Paris, France

[21] Appl. No.: 461,015

[22] Filed: Jun. 5, 1995

[30] Foreign Application Priority Data

Jun. 3, 1994 [FR] France .................. 94 06830

[51] Int. Cl.$^6$ .................. A61K 7/42; A61K 31/60
[52] U.S. Cl. .................. 424/59; 424/60; 424/400; 424/401; 514/159
[58] Field of Search .................. 424/59, 600, 400, 424/401; 514/159

[56] References Cited

FOREIGN PATENT DOCUMENTS

| | | |
|---|---|---|
| 0365370 | 4/1990 | European Pat. Off. . |
| 0521651 | 1/1993 | European Pat. Off. . |
| 2268105 | 2/1993 | France . |
| 2198944 | 6/1988 | United Kingdom . |
| 9404131 | 3/1994 | WIPO . |

OTHER PUBLICATIONS

Shaath, N., "Encyclopedi of UV absorbers for Sunscreen Products", Cosmetic & Toiletries, vol. 102, Mar. 1987, pp. 21–36.

Roelandts, R. et al, R., et al. "A Survey of Ultraviolet Absorbers in Commercially Available Sun Products", International Journal of Dermatology, 54, May 1983, vol. 22, pp. 247–255.

Langner, "*Meeting of the Society of Cometic Scientists, Jan. 1994, Teach–In*", Summary of Lecture entitled *Special Aspects of Formulating with UV Absorbers in Cosmetics & Toiletries.*

Seifen–Öle–Fette–Wachse, No. 7, 1980.

*Primary Examiner*—Shelley A. Dodson
*Attorney, Agent, or Firm*—Burns, Doane, Swecker & Mathis, L.L.P.

[57] ABSTRACT

Topically applicable sunscreen/cosmetic compositions well suited for enhanced photoprotection of human skin and/or hair against the damaging effects of UV-A and UV-B irradiation, particularly solar radiation, comprise (i) a photoprotecting effective amount of at least one of the sunscreen compounds 4-methylbenzylidenecamphor and/or 4-(tert-butyl)-4'-methoxydibenzoylmethane and (ii) at least one homomenthyl and/or octyl salicylate sunscreen solvent, in an amount sufficient to substantially completely dissolve the total amount of the at least one sunscreen compound (i), in a cosmetically acceptable vehicle, diluent or carrier therefore.

24 Claims, No Drawings

PHOTOPROTECTIVE/COSMETIC COMPOSITIONS COMPRISING AT LEAST ONE SOLID ORGANIC SUNSCREEN COMPOUND AND SALICYLATE SOLVENTS THEREFOR

CROSS-REFERENCE TO COMPANION APPLICATIONS

Copending applications
[Attorney Docket No. 016800-028], Ser. No. 08/463,221
[Attorney Docket No. 016800-029], Ser. No. 08/463,505
[Attorney Docket No. 016800-030], Ser. No. 08/463,503 U.S. Pat. No. 5,489,431
[Attorney Docket No. 016800-031], Ser. No. 08/463,762
[Attorney Docket No. 016800-032], Ser. No. 08/463,304
[Attorney Docket No. 016800-033], Ser. No. 08/463,508
[Attorney Docket No. 016800-035], Ser. No. 08/463,507
[Attorney Docket No. 016800-036], Ser. No. 08/464,940
each filed concurrently herewith and each assigned to the assignee hereof.

BACKGROUND OF THE INVENTION

1. Technical Field of the Invention

The present invention relates to novel cosmetic compositions for topical application, for the photoprotection of the skin and/or the hair against ultraviolet radiation (such compositions hereinafter simply designated "sunscreen," "sunscreen/cosmetic" or "photoprotective/sunscreen" compositions), and to the use of same for the cosmetic applications indicated above.

This invention more especially relates to the aforesaid sunscreen/cosmetic compositions comprising, in a cosmetically acceptable vehicle, carrier or diluent, typically an oil-in-water emulsion, combinatory immixture of (i) at least one of two particular solid lipophilic organic sunscreen compounds and (ii) at least one of two particular liquid lipophilic salicylate sunscreen compounds that solubilize said solid sunscreen compounds (i) therein.

2. Description of the Prior Art

It is well known to this art that light radiation of wavelengths of from 280 nm to 400 nm promotes tanning of the human epidermis, and that irradiation of wavelengths of from 280 to 320 nm, i.e., UV-B irradiation, causes erythema and burning of the skin which can impair the development of a natural tan; hence, such UV-B radiation must thus be screened from the skin.

It is also known to this art that UV-A radiation, of wavelengths from 320 to 400 nm, which tans the skin, also adversely affects it, in particular in the event of sensitive skin or a skin which is continually exposed to solar radiation.

UV-A rays cause, in particular, a loss in the elasticity of the skin and the appearance of wrinkles, promoting a premature aging thereof. Such irradiation promotes triggering of the erythematous reaction or enhances this reaction in certain individuals, and may even be the source of phototoxic or photoallergic reactions. Thus, it is desirable to also screen out UV-A radiation.

A wide variety of cosmetic compositions intended for the photoprotection (UV-A and/or UV-B) of human skin are known to this art.

These photoprotective/sunscreen compositions are typically oil-in-water emulsions (namely, a cosmetically acceptable vehicle, carrier or diluent comprising an aqueous continuous dispersing phase and an oily discontinuous dispersed phase) which contains, in various concentrations, one or more standard lipophilic and/or hydrophilic organic sunscreen compounds capable of selectively absorbing harmful or deleterious UV radiation. These sunscreen compounds (and the amounts thereof) are selected as a function of the desired sun protection factor (the sun protection factor (SPF) being expressed mathematically by the ratio of the irradiation time required to attain the erythema-forming threshold with the UV screening agent to the time required to attain the erythema-forming threshold in the absence of UV screening agent).

Two organic sunscreen compounds having desirable properties and which to date have been widely used are (1) 4-methylbenzylidenecamphor, which is commercially available and marketed under the trademark "EUSOLEX 6300" by Merck, and (2) 4-(tert-butyl)-4'-methoxydibenzoylmethane, also available commercially and marketed under the trademark "PARSOL 1789" by Givaudan.

These are two lipophilic sunscreen compounds, the first of which is highly active in the UV-B range and the second of which is highly active in the UV-A range, but which present the disadvantage of both being solid at room temperature. For this reason, incorporating same into sunscreen/cosmetic compositions, whether alone or in admixture, entails certain constraints as regards their formulation and application, in particular in the selection of the solvents permitting proper dissolution thereof. In this respect, solvent oils are typically employed, such as esters and in particular $C_{12}$–$C_{15}$ alkyl benzoates ("Finsolv TN" marketed by Finetex), or triglycerides and in particular triglycerides of $C_8$–$C_{12}$ fatty acids ("Miglyol 812" marketed by Hüls), or, alternatively, of monoalcohols or polyols such as ethanol, or mixtures thereof. These oils nevertheless present certain disadvantages, in particular they exhibit no specific (or intrinsic) activity in respect of screening UV radiation (whether UV-A and/or UV-B), even though their solubilizing properties vis-a-vis the aforesaid two sunscreen compounds are adequate.

SUMMARY OF THE INVENTION

It has now unexpectedly and surprisingly been determined that homomenthyl salicylate (also known more simply as "homosalate") and octyl salicylate, as well as mixtures thereof, are conspicuously very good solvents for the two solid sunscreen compounds indicated above, namely, 4-methylbenzylidenecamphor and/or 4-(tert-butyl)-4'-methoxydibenzoylmethane. Indeed, these solid lipophilic sunscreen compounds exhibit extremely high solubilities in the aforesaid salicylate compounds, which solubilities are, in all instances, markedly superior than those obtained using the other conventional solvents to date characterizing the state of this art. It is thus possible, with an equal amount of solvent, to formulate greater amounts of the solid sunscreen compounds.

It should also be appreciated that homomenthyl salicylate, on the one hand, and octyl salicylate, on the other, are liquid lipophilic screening compounds already known to be active in the UV-B range, but their solubilizing properties in respect of the above solid sunscreen compounds have never been described.

Thus, the advantages of the present invention are manifold in that not only can the 4-methylbenzylidenecamphor and 4-(tert-butyl)-4'-methoxydibenzoylmethane, or mixture thereof, be solubilized in a novel solvent, itself per se advantageous, but also, at the same time, a substantial increase is provided, at an equal concentration of the aforesaid two sunscreen compounds in the final sunscreen/cosmetic composition, in the level of photoprotection imparted thereby.

Briefly, the present invention features novel photoprotective/cosmetic compositions comprising, in a cosmetically acceptable vehicle, diluent or carrier, (i) an effective sunscreen amount of 4-methylbenzylidenecamphor and/or 4-(tert-butyl-4'-methoxydibenzoylmethane, and (ii) an amount of at least one of the solvents, homomenthyl salicylate, octyl salicylate, or mixture thereof, to effectively solubilize the total amount of solid sunscreen compounds (i) contained therein.

The present invention also features the use of such compositions as, or for the formulation of, sunscreen/cosmetic compositions intended for the photoprotection of the skin and/or the hair against ultraviolet irradiation, in particular solar radiation.

The cosmetic treatment for the photoprotection of the skin and/or the hair against ultraviolet irradiation, in particular solar radiation, comprises topically applying thereto an effective amount of a sunscreen/cosmetic composition as described above.

This invention, thus, also features the use of homomenthyl salicylate and/or octyl salicylate as solvent(s) in sunscreen/cosmetic compositions comprised of 4-methylbenzylidenecamphor and/or 4-(tert-butyl)-4'-methoxydibenzoylmethane.

DETAILED DESCRIPTION OF BEST MODE AND PREFERRED EMBODIMENTS OF THE INVENTION

More particularly according to the present invention, as indicated bove, 4-methylbenzylidenecamphor (compound A to be solubilized) is a sunscreen compound that is per se known to this art and is active in the UV-B range, is a solid material and is marketed commercially under the trademark "EUSOLEX 6300" by Merck and under the trademark "PARSOL 5000" by Givaudan. This compound has the following structural formula (I):

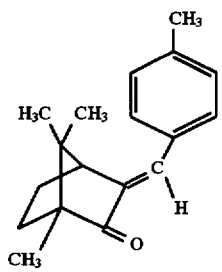

Similarly the 4-(tert-butyl)-4'-methoxydibenzoylmethane (compound B to be solubilized) is a solid sunscreen compound active in the UV-A range and is also per se known to this art; it too is available commercially under the trademark "PARSOL 1789" by Givaudan. This compound B has the following structural formula (II):

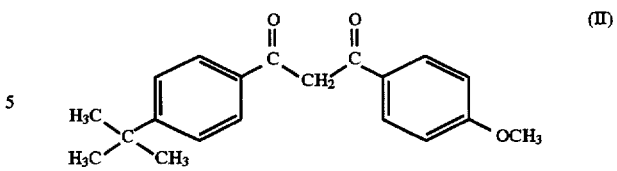

The homomenthyl salicylate (compound C, a solvent for the compounds A and/or B), also known as "homosalate," is also commercially available and is marketed, in particular, under the trademark "Kemester HMS" by Witco. It has the following structural formula (III):

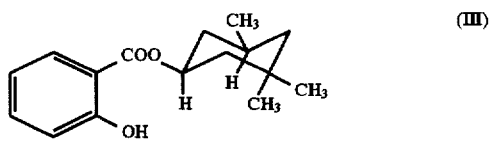

The octyl salicylate (compound D, also a solvent, whether or not jointly with the other solubilizing compound C, for the compounds A and/or B) is marketed, in particular, under the trademark "UVINUL O-18" by BASF. It has the following structural formula (IV):

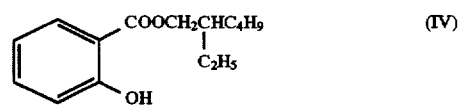

The compounds A and/or B (solid sunscreen compounds to be solubilized) are advantageously present in the sunscreen/cosmetic compositions according to the invention at a concentration ranging from 0.25% to 15% by weight relative to the total weight of the composition. In an essential embodiment of the present invention, these compounds A and/or B must exist in the final sunscreen/cosmetic composition in a totally, or substantially totally, solubilized (dissolved) state.

The compounds C and/or D (solubilizing agents) are themselves advantageously present in the sunscreen/cosmetic compositions according to the invention at a concentration ranging from 0.5% to 20% by weight relative to the total weight of the composition. In a particularly preferred and advantageous embodiment of the invention, these compounds C and/or D are employed in amounts sufficient to themselves dissolve the total amount, or substantially the total amount, of the compounds A and/or B present in the composition. This minimum amount of solvent(s) for the complete and stable dissolution of the solid sunscreen compounds (i) can readily be determined from the solubility parameters of said screening compounds in these solvents.

For example, at room temperature, the compound A is soluble in a proportion of 40% by weight in the solvent compound C, and in an amount of 50% by weight in the solvent compound D. The compound B is itself soluble in a proportion of 50% by weight in the solvent compound C, and in an amount of 30% by weight in the solvent compound D. Also, a mixture comprising compound A and compound B in a 3:1 weight ratio is soluble in a proportion of 55% by weight in the solvent compound C, and in an amount of 57% by weight in the solvent compound D.

Moreover, the concentrations and ratios of the compounds A and/or B and of the compounds C and/or D are typically selected such that the sun protection factor of the final composition is preferably at least 2.

In another particularly preferred embodiment of the invention, the final sunscreen/cosmetic compositions preferably contain no, or substantially no, solubilizing agent for the compounds A, B or (A+B) other than the compound or compounds C and D described above. According to the invention, a given compound is considered as not possessing any solubilizing properties with respect to another given compound when the latter compound has a solubility of less than approximately 1% by weight in the first compound.

In another preferred embodiment of the present invention, the cosmetically acceptable vehicle, diluent, carrier or support in which the various compounds A, B, C and D are formulated is an emulsion of oil-in-water type.

In yet another particularly preferred embodiment of the present invention, the sunscreen compounds A and B in the solubilized state provide a mixture of a UV-B sunscreen compound, i.e., the 4-methylbenzylidenecamphor, and a UV-A sunscreen compound, i.e., the 4-(tert-butyl)-4'-methoxydibenzoylmethane. Thus, improved sunscreen/cosmetic formulations are provided which offer maximum photoprotection throughout the harmful UV range (280 nm–400 nm), and these formulations are moreover perfectly stable.

Of course, the sunscreen/cosmetic compositions according to the invention may contain one or more additional hydrophilic or lipophilic sunscreen agents active in the UV-A and/or UV-B range (absorbers), other than the two sunscreen compounds indicated above. Exemplary of such additional sunscreens are cinnamic derivatives, salicylic derivatives, camphor derivatives, triazine derivatives, benzophenone derivatives, dibenzoylmethane derivatives, β,β-diphenylacrylate derivatives, p-aminobenzoic acid derivatives, and the sunscreen polymers and sunscreen silicones described in WO-93/04,665. Other examples of organic sunscreen agents are described in EO-A-0,487,404.

The compositions according to the invention may also contain agents for the artificial tanning and/or browning of the skin (self-tanning agents) such as, for example, dihydroxyacetone (DHA).

The cosmetic compositions according to the invention may also contain pigments or, alternatively, nanopigments (average size of the primary particles: generally ranging from 5 nm to 100 nm, preferably from 10 to 50 nm) of coated or uncoated metal oxides such as, for example, nanopigments of titanium dioxide (amorphous or crystallized in rutile and/or anatase form), of iron oxide, of zinc oxide, of zirconium oxide or of cerium oxide, which are all photoprotective agents that are per se well known to this art and which are effective by physical blocking (reflection and/or diffusion) of the UV irradiation. Conventional coating agents include, moreover, alumina and/or aluminum stearate. Such coated or uncoated metal oxide nanopigments are described, in particular, in EP-A-0,518,772 and EP-A-0,518,773.

The compositions of the invention may additionally comprise conventional cosmetic additives and adjuvants selected especially from among fats, organic solvents, ionic or nonionic thickening agents, softeners, antioxidants and especially anti-free-radical antioxidants, opacifying agents, stabilizing agents, emollients, silicones, α-hydroxy acids, antifoaming agents, hydrating agents, vitamins, fragrances, preservatives, surfactants, fillers, insect repellants, sequestering agents, polymers, propellants, basifying or acidifying agents, dyes and colorants, or any other ingredient usually employed in cosmetics, in particular for the production of sunscreen/cosmetic compositions in emulsion form.

The fats may comprise an oil or a wax or mixtures thereof, and may also comprise fatty acids, fatty alcohols and fatty acid esters. The oils may be selected from among animal, plant, mineral or synthetic oils and, especially, from among liquid petrolatum, paraffin oil, volatile or non-volatile silicone oils, isoparaffins, poly-α-olefins, fluoro oils and perfluoro oils. Similarly, the waxes may be selected from among animal, fossil, plant, mineral or synthetic waxes that are per se known to this art.

Exemplary organic solvents include the lower polyols and alcohols.

The thickening agents may be selected, especially, from among crosslinked polyacrylic acids, modified or unmodified guar gums and celluloses such as hydroxypropyl guar gum, methylhydroxyethylcellulose and hydroxypropylmethylcellulose.

The compositions of the invention may be formulated according to techniques well known to this art, in particular those intended for the preparation of emulsions of oil-in-water or water-in-oil type.

The subject compositions may, in particular, be in simple or complex (O/W, W/O, O/W/O or W/O/W) emulsion form such as a cream, a milk, a gel, an ointment or a cream gel, in powder form or in solid stick form and may optionally be packaged as an aerosol and may be provided in the form of a foam or a spray.

When it is an emulsion, the aqueous phase of this emulsion may comprise a nonionic vesicle dispersion prepared according to known processes (Bangham, Standish and Watkins, J. Mol. Biol, 13, 238 (1965), FR-2,315,991 and FR-2,416,008).

The cosmetic compositions of the invention are useful for protecting the human epidermis or the hair against the damaging effects of ultraviolet rays, as sunscreen compositions or as makeup products.

When the cosmetic compositions according to the invention are used for photoprotection of the human epidermis against UV rays, or as sunscreen compositions, they may be formulated as a suspension or a dispersion in solvents or fats, in the form of a nonionic vesicle dispersion or, alternatively, in the form of an emulsion, preferably of oil-in-water type, such as a cream or a milk, or in ointment, gel, cream gel, solid stick, stick, aerosol foam or spray form.

When the cosmetic compositions according to the invention are used for the photoprotection of the hair, they may be formulated as a shampoo, a lotion, a gel, an emulsion, a nonionic vesicle dispersion or a lacquer for the hair and may constitute, for example, a composition to be rinsed, to be applied before or after shampooing, before or after dyeing or bleaching, before, during or after permanent-waving or hair-straightening, a styling or treating lotion or gel, a blow-drying or hair-setting lotion or gel, or a composition for the permanent-waving or straightening, dyeing or bleaching of the hair.

When the subject compositions are used as a makeup product for the eyelashes, the eyebrows or the skin, such as an epidermal treatment cream, a foundation, a lipstick, an eyeshadow, a blush, a mascara or "eyeliner", they may be in anhydrous or aqueous, solid or pasty form, such as oil-in-water or water-in-oil emulsions, nonionic vesicle dispersions or, alternatively, suspensions.

For example, for the photoprotective/sunscreen formulations in accordance with this invention which comprise a vehicle of oil-in-water emulsion type, the aqueous phase (comprising hydrophilic sunscreen agents in particular) generally constitutes from 50% to 95% by weight, preferably from 70% to 90% by weight, relative to the total formulation, the oily phase (comprising lipophilic sunscreen agents in particular) from 5% to 50% by weight, preferably from 10% to 30% by weight, relative to the total formulation, and the (co)emulsifying agent(s) from 0.5% to 20% by weight, preferably from 2% to 10% by weight, relative to the total formulation. If desired, the fatty phase of the emulsions according to the invention may comprise only or essentially only the salicylates C and/or D (organic solvents/sunscreens) in which the compounds A and/or B are dissolved, together with the optional additional screening agents and other conventional lipophilic cosmetic additives and adjuvants.

The cosmetic treatment of the skin or hair to protect same against the deleterious effects of UV rays, especially those contained in solar radiation, comprises applying thereto an effective amount of a sunscreen/cosmetic composition as described above.

In order to further illustrate the present invention and the advantages thereof, the following specific examples are given, it being understood that same are intended only as illustrative and in nowise limitative.

EXAMPLE 1

Oil-in-Water Emulsion

| | |
|---|---|
| (a) 4-Methylbenzylidenecamphor ("EUSOLEX 6300") | 6 g |
| (b) 4-(tert-butyl)-4'-methoxydibenzoylmethane ("PARSOL 1789") | 2 g |
| (c) Homomenthyl salicylate | 10 g |
| (d) TiO$_2$ of nanopigment grade | 4 g |
| (e) Mixture of cetylstearyl alcohol and oxyethylenated cetylstearyl alcohol containing 33 moles of ethylene oxide, marketed under the trademark "SINNOWAX AO" by Henkel (emulsifying agent) | 7 g |
| (f) Mixture of glyceryl mono-, di- and tristearate (co-emulsifying agent) | 2 g |
| (g) C$_8$–C$_{12}$ fatty acid triglycerides ("MIGLYOL 812") | 3 g |
| (h) Polydimethylsiloxane | 1.5 g |
| (i) Cetyl alcohol | 1.5 g |
| (j) Preservatives | qs |
| (k) Distilled water | qs 100 g |

The above emulsion was prepared by dissolving the photoprotective/sunscreen agents into the fatty phase and then adding the (co)emulsifying agents into this fatty phase, heated to about 80° C., and, lastly, adding the water, preheated to this same temperature, with rapid stirring.

EXAMPLE 2

Oil-in-Water Emulsion

| | |
|---|---|
| (a) 4-Methylbenzylidenecamphor ("EUSOLEX 6300") | 3 g |
| (b) 4-(tert-butyl)-4'-methoxydibenzoylmethane ("PARSOL 1789") | 1 g |
| (c) Octyl salicylate | 8 g |
| (d) Benzene-1,4-[di(3-methylidene-camphor-10-sulfonic] acid | 1.5 g |
| (e) Mixture of cetylstearyl alcohol and oxyethylenated cetylstearyl alcohol containing 33 moles of ethylene oxide, marketed under the trademark "SINNOWAX AO" by Henkel (emulsifying agent) | 7 g |
| (f) Mixture of glyceryl mono-, di- and tristearate (co-emulsifying agent) | 2 g |
| (g) C$_8$–C$_{12}$ fatty acid triglycerides ("MIGLYOL 812") | 3 g |
| (h) Polydimethylsiloxane | 1.5 g |

-continued

| | |
|---|---|
| (i) Cetyl alcohol | 1.5 g |
| (j) Preservatives | qs |
| (k) Distilled water | qs 100 g |

The above emulsion was prepared as in Example 1.

EXAMPLE 3

Water-in-Oil Emulsion

| | |
|---|---|
| (a) 4-Methylbenzylidenecamphor ("EUSOLEX 6300") | 6 g |
| (b) 4-(tert-butyl)-4'-methoxydibenzoylmethane ("PARSOL 1789") | 2 g |
| (c) Octyl salicylate | 8 g |
| (d) Homomenthyl salicylate | 5 g |
| (e) [Glyceryl and sorbitol hydroxystearate and isostearate] mixture containing 20 moles of propylene oxide and 30 moles of ethylene oxide, marketed under the trademark "ARLACEL 780" by ICI | 2.5 g |
| (f) Preservatives | qs |
| (g) Fragrance | qs |
| (h) Water | qs 100 g |

While the invention has been described in terms of various preferred embodiments, the skilled artisan will appreciate that various modifications, substitutions, omissions, and changes may be made without departing from the spirit thereof. Accordingly, it is intended that the scope of the present invention be limited solely by the scope of the following claims, including equivalents thereof.

What is claimed is:

1. A topically applicable sunscreen/cosmetic composition adopted for the photoprotection of human skin and/or hair, comprising (i) a photoprotecting effective amount of at least one of the sunscreen compounds 4-methylbenzylidenecamphor and/or 4-(tert-butyl)-4'-methoxydibenzoylmethane and (ii) at least one homomenthyl and/or octyl salicylate sunscreen solvent, wherein said solvent, by itself, is contained in an amount sufficient to substantially completely dissolve the total amount of said at least one sunscreen compound (i), in a cosmetically acceptable vehicle, diluent or carrier therefor.

2. The sunscreen/cosmetic composition as defined by claim 1, comprising (i) a photoprotecting effective amount of a mixture of said 4-methylbenzylidenecamphor compound and said 4-(tert-butyl)-4'-methoxydibenzoylmethane compound.

3. The sunscreen/cosmetic composition as defined by claim 1, substantially devoid of any solvent for said at least one sunscreen compound (i), other than said at least one homomenthyl and/or octyl salicylate solvent (ii).

4. The sunscreen/cosmetic composition as defined by claim 1, comprising from 0.25% to 15% by weight of said at least one sunscreen compound (i).

5. The sunscreen/cosmetic composition as defined by claim 4, comprising from 0.5% to 20% by weight of said at least one homomenthyl and/or octyl salicylate solvent (ii).

6. The sunscreen/cosmetic composition as defined by claim 1, comprising an oil-in-water emulsion.

7. The sunscreen/cosmetic composition as defined by claim 1, comprising a water-in-oil emulsion.

8. The sunscreen/cosmetic composition as defined by claim 1, further comprising at least one additional hydrophilic or lipophilic organic UV-A and/or UV-B sunscreen.

9. The sunscreen/cosmetic composition as defined by claim 8, further comprising at least one cinnamic derivative, salicylic derivative, camphor derivative, triazine derivative, benzophenone derivative, dibenzoylmethane derivative, β,β-diphenylacrylate derivative, p-aminobenzoic acid derivative, sunscreen polymer, or sunscreen silicone.

10. The sunscreen/cosmetic composition as defined by claim 1, further comprising a photoprotecting effective amount of particulates of at least one inorganic pigment or nanopigment.

11. The sunscreen/cosmetic composition as defined by claim 10, said at least one pigment or nanopigment comprising titanium dioxide, zinc oxide, iron oxide, zirconium oxide, cerium oxide, or mixture thereof.

12. The sunscreen/cosmetic composition as defined by claim 1, further comprising at least one active agent for the artificial tanning and/or browning of human skin.

13. The sunscreen/cosmetic composition as defined by claim 1, further comprising at least one cosmetically acceptable adjuvant or additive.

14. The sunscreen/cosmetic composition as defined by claim 13, said at least one adjuvant or additive comprising a fat, organic solvent, ionic or nonionic thickening agent, softener, antioxidant, anti-free-radical antioxidant, opacifying agent, stabilizing agent, emollient, silicone, α-hydroxy acid, anti-foaming agent, hydrating agent, vitamin, fragrance, preservative, surfactant, filler, sequestering agent, polymer, propellant, insect repellent, basifying or acidifying agent, dye, colorant, or mixture thereof.

15. The sunscreen/cosmetic composition as defined by claim 1, comprising a nonionic vesicle dispersion, emulsion, cream, milk, gel, cream gel, ointment, suspension, dispersion, powder, solid stick, foam or spray.

16. The sunscreen/cosmetic composition as defined by claim 1, comprising a makeup.

17. The sunscreen/cosmetic composition as defined by claim 16, comprising an anhydrous or aqueous solid or paste, emulsion, suspension, or dispersion.

18. The sunscreen/cosmetic composition as defined by claim 1, comprising a shampoo, lotion, gel, emulsion, nonionic vesicle dispersion, hair lacquer, or rinse.

19. The sunscreen/cosmetic composition as defined by claim 1, having a sun protection factor of at least 2.

20. A method for protecting human skin and/or hair against the deleterious effects of ultraviolet irradiation, comprising topically applying thereto an effective amount of the sunscreen/cosmetic composition as defined by claim 1.

21. A method for protecting human skin and/or hair against the deleterious effects of solar radiation, comprising topically applying thereto an effective amount of the sunscreen/cosmetic composition as defined by claim 1.

22. The composition of claim 1, wherein the only solvent present is homomenthyl salicylate.

23. The composition of claim 22, wherein the amount of said solvent ranges from 0.5% to 20% by weight of said compound.

24. A method for protecting human hair and/or skin against the deleterious effects of solar radiation comprising topically applying thereto an effective amount of a sunscreen/cosmetic composition according to claim 22.

* * * * *